United States Patent [19]
Hakim et al.

[11] 3,958,562
[45] May 25, 1976

[54] IMPLANTABLE PRESSURE SENSOR

[75] Inventors: Salomon Hakim, Bogota, Colombia;
Donald L. Harris, Miami Beach, Fla.

[73] Assignee: Hakim Company Limited, Saint Vincent, British W. Indies

[22] Filed: Dec. 2, 1974

[21] Appl. No.: 528,661

Related U.S. Application Data

[62] Division of Ser. No. 474,518, May 30, 1974, Pat. No. 3,877,137.

[52] U.S. Cl. .......................... 128/2 R; 128/2.05 E; 128/DIG. 21
[51] Int. Cl.² ........................................... A61B 5/00
[58] Field of Search .............. 128/2 A, 2 R, 2.05 E, 128/350 R, 350 V, DIG. 21; 210/507

[56] References Cited
UNITED STATES PATENTS

| | | | |
|---|---|---|---|
| 2,528,847 | 11/1950 | Van Norden | 210/507 X |
| 3,111,125 | 11/1963 | Schulte | 128/350 V |
| 3,310,051 | 3/1967 | Schulte | 128/350 R X |
| 3,625,100 | 12/1971 | Summers | 128/2 R |
| 3,669,094 | 6/1972 | Heyer | 128/350 R X |
| 3,750,194 | 8/1973 | Summers | 128/350 R |
| 3,765,414 | 10/1973 | Arlen | 128/350 R X |

FOREIGN PATENTS OR APPLICATIONS

| | | | |
|---|---|---|---|
| 70,354 | 11/1915 | Germany | 210/507 |

*Primary Examiner*—Kyle L. Howell
*Attorney, Agent, or Firm*—Kenway & Jenney

[57] ABSTRACT

In the implantable pressure sensor disclosed herein, a radio-opaque liquid is contained within a resiliently compressible vessel of a silicone rubber, the volume of liquid actually contained within the vessel being then variable as a function of the pressure or force applied to the vessel. The silicone rubber is rendered impervious to the radio-opaque liquid by a treatment which involves expandng and saturating the cured silicone rubber with a mixture of a hydrocarbon solvent such as heptane containing a dissolved wax such as beeswax. The solvent expands and saturates the silicone rubber, carrying beeswax into the silicone rubber. When the solvent evaporates, the beeswax is then trapped within the interstices of the silicone rubber, under tension.

3 Claims, 2 Drawing Figures

IMPLANTABLE PRESSURE SENSOR

This is a division of application Ser. No. 474,518 filed May 30, 1974, now U.S. Pat. No. 3,877,137.

BACKGROUND OF THE INVENTION

This invention relates to an implantable pressure sensor.

In various medical diagnostic and treatment techniques, it is desirable to measure and/or sense pressures and forces within the body of the patient. For example, in patients with hydrocephalus, it may be highly useful to know the hydrostatic pressure of CSF (cerebral spinal fluid) within the ventricles inside the patient's skull. Likewise, in the treatment of hydrocephalus, it is useful to sense the force or pressure exerted by the brain against the skull and to control the venting of CSF from the ventricles in accordance with the techniques disclosed in the application of Salomon Hakim entitled Ventricular Shunt Having a Variable Pressure Valve, Ser. No. 280,451 filed August 14, 1972, now abandoned.

Among the several objects of the present invention may be noted the provision of a pressure sensor which is implantable within a patient undergoing diagnosis or treatment; the provision of such a sensor which employs only materials which are nonreactive with body fluids; the provision of such a sensor which is reliable and long-lived and which is of relatively simple and inexpensive construction. Other objects and features will be in part apparent and in part pointed out hereinafter.

SUMMARY OF THE INVENTION

Briefly, an implantable pressure sensor in accordance with the present invention comprises a vessel of a silicone rubber material which can be compressed by applied force or pressure. The vessel contains a filling of a fluid which can be displaced by such compression, the fluid preferably being a non-toxic, radio-opaque material. The walls of the silicone rubber material are rendered substantially impervious to the fluid by soaking the cured silicone rubber material in a mixture of hydrocarbon solvent and a wax. After the solvent is allowed to evaporate, the wax is held by tension in the silicone rubber matrix, rendering the vessel substantially impervious to the liquid.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
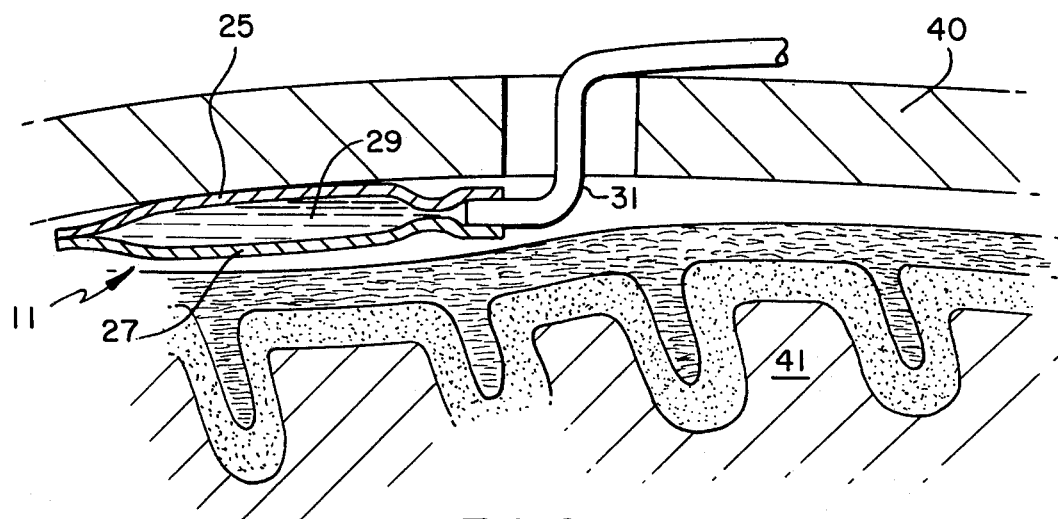
FIG. 1 is a side view, in section, of an implanted pressure-measuring sensor in accordance with the present invention.

Referring now to FIG. 1, there is indicated at 11 a compressible vessel in the form of a bulb or bladder constructed of Silastic, i.e. silicone rubber. The vessel may be formed by joining, around their peripheries, a pair of disk-like sheets of silicone rubber material 25 and 27, the intermediate space being filled with a suitable hydraulic fluid 29 which is preferably radio-opaque. At one side of the sensor, the space between the sheets 25 and 27 communicates with a tube or conduit 31 through which pressures or forces sensed by the bladder may be communicated to apparatus for utilizing fluid displaced from the vessel by applied pressure or force.

A preferred use for the sensor of FIG. 1 is as a pressure or force sensor in a hydraulic servo system i.e. of the type disclosed in application Ser. No. 280,451, referred to previously. The vessel 11 may be implanted between the skull 40 and brain 41 of a patient suffering from hydrocephalus with the tubing 31 leading outside the skull, as indicated. In such a case, the displaced liquid may operate a bellows which affects the operation of a servo-valve, as discloosed in said pending application.

A suitable material for the sheets 25 and 27 is Dow Corning MDX–4–4514, assembly being with Dow Corning Silastic medical adhesive Type A. These same materials may also be used for forming conduits and other components of the servo-valve system.

Figure 2:
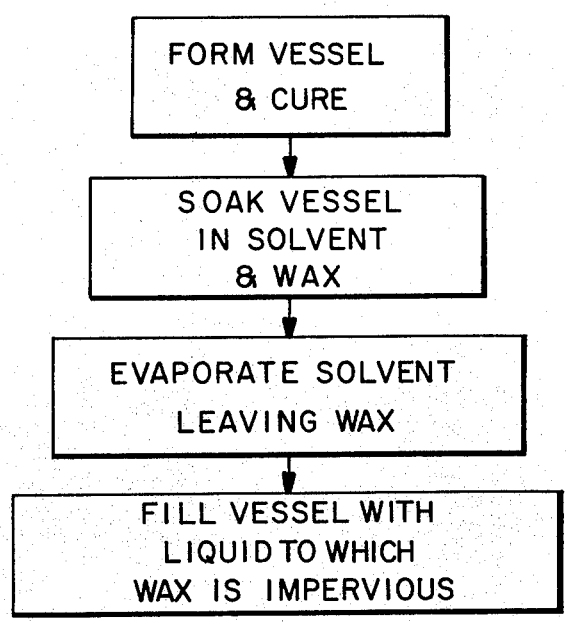
FIG. 2 is a chart illustrating steps in a process of treating a silastic material in accordance with the present invention.

A preferred radio-opaque material with which to fill the vessels of FIGS. 1 and 2 is Lipiodol F, a contrast medium manufactured and sold as an article of commerce by:

Laboratoiers André Guerbert & Cie A. Guerbert Pharmacien 22, Rue Du Landy Saint Quen, Paris, Mon 2256

This material is a popular contrast media employed in mielography and, as is understood by those skilled in the art, is essentially non-toxic and non-reactive with body fluids, being in fact injectable directly into the cerebrospinal fluid of the patient's spinal subarachnoid space or ventricular cavities for contrast studies. Similar such media are known in the art, e.g. ethyl iodophenyl undecylate.

To render the walls of the silicone rubber vessel impervious to the radio-opaque liquid, the silicone rubber is impregnated with a wax which is impervious to the liquid by a method which effectively encapsulates the wax under tension in the silastic matrix, as illustrated in FIG. 2. In the case of Lipiodol F, the preferred radio-opaque liquid, a preferred wax is beeswax.

To treat a silicone rubber vessel, the vessel is soaked in a mixture of the wax in a suitable hydrocarbon solvent. In the case of the beeswax which is used with Lipiodol F, a suitable solvent is heptane. The solvent substantially expands the silicone rubber matrix and the wax which is dissolved in the solvent permeates substantially throughout the walls of the vessel. After thorough soaking, the silicone rubber vessel is removed from the solvent mixture and the solvent is allowed to evaporate. Upon evaporation of the solvent, the silicone rubber tends to contract toward its original size, effectively encapsulating the wax in the interstices of the silicone rubber matrix, the wax being under compression while the silicone rubber material itself is under tension. Encapsulating the wax by this method renders the silicone rubber material substantially impervious to the radio-opaque liquid for an indefinite period, so that the sensors are suitable for implantation and are able to function for usefully long periods, barring physical damage.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. An implantable pressure sensor comprising:
   a silicone rubber vessel the walls of which include wax trapped within the silicone rubber, the silicone rubber completely encasing the wax;
   within said vessel, a filling of a non-toxic hydraulic fluid which is compatible with body fluids; and
   coupled to said vessel, means for accomodating fluid displaced from said vessel when said vessel is subjected to pressure.

2. An implantable pressure sensor as set forth in claim 1 wherein said fluid is a radio-opaque injection contrast media.

3. An implantable pressure sensor comprising:
   a silicone rubber vessel the walls of which include beeswax trapped within the silicone rubber, the silicone rubber being in tension around the beeswax;
   within said vessel, a filling of the liquid, Lipiodol F; and
   coupled to said vessel, means for accomodating fluid displaced from said vessel when said vessel is subjected to pressure.

* * * * *